(12) United States Patent
Cho

(10) Patent No.: US 9,078,623 B2
(45) Date of Patent: Jul. 14, 2015

(54) MULTIPLE-ENERGY X-RAY IMAGING SYSTEM AND CONTROL METHOD FOR THE SAME

(75) Inventor: Min Kook Cho, Gyeonggi-do (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 0 days.

(21) Appl. No.: 13/533,095

(22) Filed: Jun. 26, 2012

(65) Prior Publication Data
US 2013/0022168 A1 Jan. 24, 2013

(30) Foreign Application Priority Data

Jul. 19, 2011 (KR) ......................... 10-2011-0071619

(51) Int. Cl.
*A61B 6/00* (2006.01)

(52) U.S. Cl.
CPC .................. *A61B 6/541* (2013.01); *A61B 6/482* (2013.01); *A61B 6/405* (2013.01)

(58) Field of Classification Search
CPC ................................ A61B 6/482; A61B 6/541
See application file for complete search history.

(56) References Cited

U.S. PATENT DOCUMENTS

| 7,596,206 B2 * | 9/2009 | Fuhrmann et al. ............... 378/62 |
| 7,854,551 B2 * | 12/2010 | Lv et al. ......................... 378/189 |
| 2006/0280284 A1 | 12/2006 | Sasaki et al. |
| 2007/0041490 A1 * | 2/2007 | Jha et al. ............................ 378/8 |
| 2009/0112105 A1 * | 4/2009 | Clayman ......................... 600/509 |
| 2010/0123083 A1 * | 5/2010 | Petrick et al. ............. 250/370.09 |
| 2010/0210921 A1 * | 8/2010 | Park et al. ...................... 600/301 |

FOREIGN PATENT DOCUMENTS

JP 2006-006531 A 1/2006

* cited by examiner

*Primary Examiner* — Glen Kao
*Assistant Examiner* — Danielle Fox
(74) *Attorney, Agent, or Firm* — Cha & Reiter, LLC

(57) ABSTRACT

A multiple-energy X-ray imaging apparatus and a method obtain a plurality of X-ray images when the heart of a patient is in the same phase by measuring the electrocardiogram of the patient. A sensor is installed on a handle or a foot stool to measure the electrocardiogram when the patient grips the handle or makes contact with the foot stool without having to attach an electrode to the body of the patient, which removes the inconvenience in measuring the electrocardiogram.

19 Claims, 10 Drawing Sheets

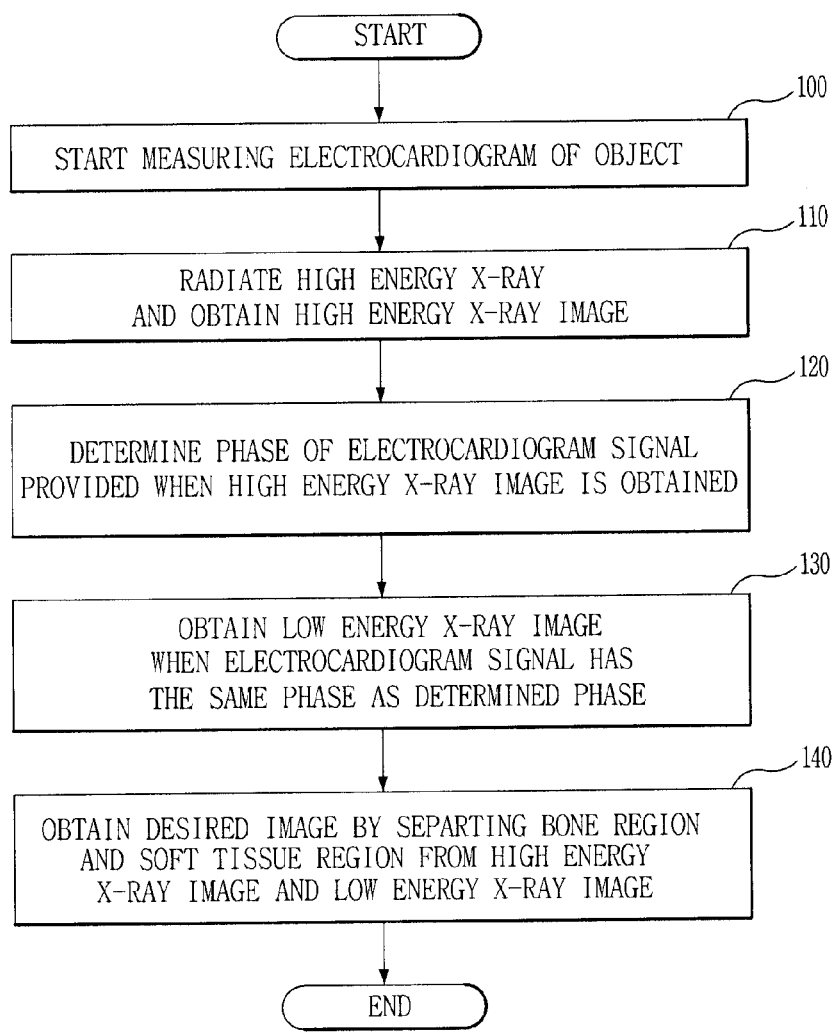

MULTIPLE-ENERGY X-RAY IMAGING SYSTEM AND CONTROL METHOD FOR THE SAME

CLAIM OF PRIORITY

This application claims, pursuant to 35 U.S.C. §119(a), priority to and the benefit of Korean Patent Application No. 10-2011-0071619, filed on Jul. 19, 2011 in the Korean Intellectual Property Office, the disclosure of which is incorporated herein by reference.

BACKGROUND OF THE INVENTION

1. Field of the Invention

The present invention relates to a multiple-energy X-ray imaging apparatus for obtaining an X-ray transmission image of an object by use of a plurality of X-rays having different levels of energy.

2. Description of the Related Art

An X-ray imaging apparatus is an apparatus configured to recognize the inner structure of an object by radiating an X-ray to the object and analyzing the X-ray passing through the object. Since the X-ray transmission is different at each tissue of the object, the inner structure of the object can be imaged by use of an attenuation coefficient that is obtained by quantifying the X-ray transmission.

In recent years, a multiple-energy X-ray imaging technology has been developed that uses a plurality of X-rays having different levels of energy, and many studies have been undertaken on multiple-energy X-ray imaging.

According to the methods of multiple-energy X-ray imaging, X-rays having different levels of energy are sequentially radiated to an object in order to obtain a plurality of transmission images, and images of any bone and any soft tissue are separated from the obtained transmission images, so that a clear X-ray image is obtained.

A multiple-energy X-ray image is not obtained in an instant but is obtained based on a plurality of X-ray images that are obtained by sequentially radiating a plurality of X-rays at an object, such as a patient.

Since a multiple-energy X-ray imaging apparatus sequentially obtains X-ray images, any change in breathing or the phase of a heart of a patient causes difficulty in obtaining an image under the same topological conditions, thereby degrading the precision of the X-ray imaging.

SUMMARY OF THE INVENTION

Therefore, it is an aspect of the present invention to provide a multiple-energy X-ray imaging apparatus capable of obtaining X-ray images having different energy levels when the heart of a patient is in the same phase, and a control method for the same.

Additional aspects of the invention will be set forth in part in the description which follows and, in part, will be obvious from the description, or may be learned by practice of the invention.

In accordance with one aspect of the present invention, a multiple-energy X-ray imaging apparatus includes an X-ray generating unit, a power supply unit, a detector unit, a sensor unit, and a host computer. The X-ray generating unit is configured to sequentially radiate X-rays to an object, such as a patient, starting from a first energy X-ray of first energy to a $n^{th}$ energy X-ray of $n^{th}$ energy. The power supply unit is configured to supply power to the X-ray generating unit. The detector unit is configured to detect the X-rays, which are radiated from the X-ray generating unit and pass through the object, and to convert the detected X-rays to electric signals. The sensor unit is installed on a handle grippable by the object to sense electrocardiogram signals that are generated from pulsation of a heart of the object. The host computer is configured to obtain X-ray images by performing a control procedure such that each of the X-rays starting from a second energy X-ray to the $n^{th}$ energy X-ray is sequentially radiated upon generation of an electrocardiogram signal that has the same phase as a phase of an electrocardiogram signal provided at a point of time when an image based on the first energy X-ray is obtained.

The sensor unit includes a left hand electrode making contact with a left hand of the object, a right hand electrode making contact with a right hand of the object, and a ground electrode.

The multiple-energy X-ray imaging apparatus further includes a signal processing unit configured to perform a filtering and an amplification of the electrocardiogram signal and to covert the electrocardiogram signal into a digital signal such that the electrocardiogram signal sensed by the sensor unit is analyzed.

The host computer includes a transceiver unit configured to receive X-ray signals from the detector unit, to receive an electrocardiogram signal, which has been converted into a digital signal, from the signal processing unit, and to transmit a control signal to the X-ray generating unit and the power source supply unit.

The host computer further includes an energy control unit configured to receive the electrocardiogram signals, which have been converted into digital signals, in real time and to determine an X-ray image by obtaining a time point such that the X-ray images are obtained by sequentially radiating each of the X-rays starting from the second energy X-ray to the $n^{th}$ energy X-ray upon generation of an electrocardiogram signal that has the same phase as a phase of an electrocardiogram signal provided at a point of time when an image based on the first energy X-ray is obtained.

The host computer further includes an image processing unit configured to generate a plurality of X-ray images and to separate a bone region and a soft tissue from the generated plurality of X-ray images by receiving the X-ray signals through the transceiver unit. For example, the first energy represents a high energy and the second energy represents a low energy.

In another aspect of the present invention, the sensor unit is further installed on a foot stool that makes contact with a foot of the object.

In accordance with another aspect of the present invention, a method of controlling a multiple-energy X-ray imaging apparatus is as follows.

Electrocardiogram signals of an object are measured from a sensor unit which is installed on a handle grippable by the object, such as a patient, or on a foot stool making contact with a foot of the object. A first energy X-ray image is obtained by radiating a first energy to the object. A phase of a heart of the object, at a point of time when the first energy X-ray image is obtained, is determined by analyzing the measured electrocardiogram signal. X-ray images are obtained by sequentially radiating each of X-rays starting from a second energy X-ray to a $n^{th}$ energy X-ray upon generation of an electrocardiogram signal that has the same phase as the determined phase.

Attenuation coefficients of a bone and a soft tissue are calculated from the first energy X-ray image and from subsequent X-ray images, which are obtained by sequentially radiating each of the X-rays, starting from a second energy X-ray to a $n^{th}$ energy X-ray. A bone region and a soft tissue region are separated from the obtained X-ray images by use of a difference of the calculated attenuation coefficients.

The measuring of electrocardiogram signals of the object is performed by sensing an electrocardiogram signal of the object through the sensor unit, which is installed on a dual handle that may be gripped by both hands of the object.

Alternatively, the measuring of electrocardiogram signals of the object is performed by sensing an electrocardiogram signal of the object through a sensor unit, which is installed on a handle that may be gripped by a right hand of the object, and a sensor unit, which is installed on a foot stool making contact with a left foot of the object.

In addition, the measuring of electrocardiogram signals of the object may be performed by sensing an electrocardiogram signal of the object through a sensor unit, which is installed on a handle that may be gripped by a left hand of the object, and a sensor unit, which is installed on a foot device such as a foot stool making contact with a left foot of the object.

According to the multiple-energy X-ray imaging apparatus of the present invention and the control method for the same, the phases of the heart of the object, such as a patient, are kept equal when obtaining sequential X-ray images by use of an electrocardiogram of the patient that is measured during the X-ray photography in real time, thereby removing any difference in the phases of a heart caused by the pulsation of the heart. Accordingly, an X-ray image having more precision is obtained, and precise diagnosis of the health of the object, such as a patient, is achieved.

In addition, the electrocardiogram is measured only if a patient grips a handle or the foot of a patient makes contact with a fool stool, thereby removing the inconvenience in measuring the electrocardiogram.

BRIEF DESCRIPTION OF THE DRAWINGS

These and other aspects of the invention will become apparent and more readily appreciated from the following description of exemplary embodiments of the present invention, taken in conjunction with the accompanying drawings of which:

FIG. 5 is a flowchart showing a method of controlling a multiple-energy X-ray imaging apparatus according to the exemplary embodiment of the present invention.

DETAILED DESCRIPTION OF THE INVENTION

Figure 1:
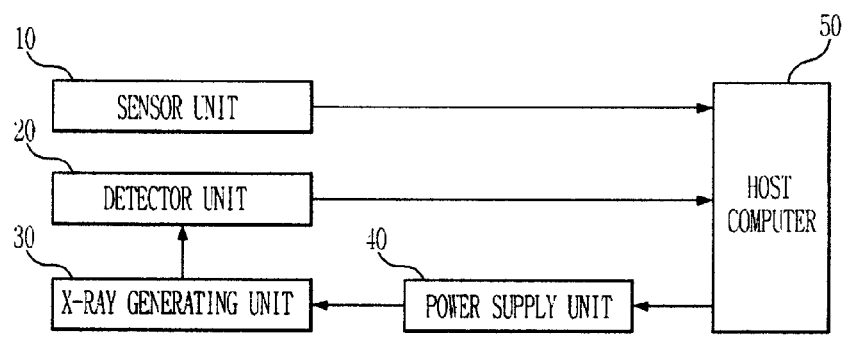
FIG. 1 is a block diagram illustrating a multiple-energy X-ray imaging apparatus according to an exemplary embodiment of the present invention.

Hereinafter, preferred embodiments of the present invention will be described with reference to the accompanying drawings, in which like reference numerals refer to like elements throughout. This invention may, however, be embodied in many different forms and should not be construed as limited to the exemplary embodiments set forth herein. In the following description, a detailed explanation of known related functions and constructions may be omitted to avoid unnecessarily obscuring the subject matter of the present invention. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

In the following description, the energy of a series of X-rays will be referred in a manner that the energy of an X-ray radiated first is denoted as a first energy and the energy of an X-ray radiated at a $n^{th}$ point of time is denoted as an $n^{th}$ energy, where n is an integer greater than 1. The first energy X-ray image represents an image obtained by radiating an X-ray having the first energy to an object, and the second energy X-ray image represents an image obtained by radiating an X-ray having the second energy to the object. The point of time at which the first energy X-ray image is obtained does not represent the point of time when an image processing finished processing an X-ray signal or image corresponding to the first energy, but instead represents the point of time when an X-ray image is obtained by radiating the X-ray having the first energy to the object. Similarly, an nth point of time at which an $n^{th}$ energy X-ray image is obtained represents when an X-ray image is obtained by radiating the X-ray with the $n^{th}$ X-ray energy.

In addition, the point of time at which the X-ray image is obtained is determined based on the electrocardiogram of an object. Accordingly, the object which is X-rayed according to the present invention represents a living body, for example, a human patient.

FIG. 1 is a block diagram illustrating a multiple-energy X-ray imaging apparatus according to a first exemplary embodiment of the present invention.

Figure 2:
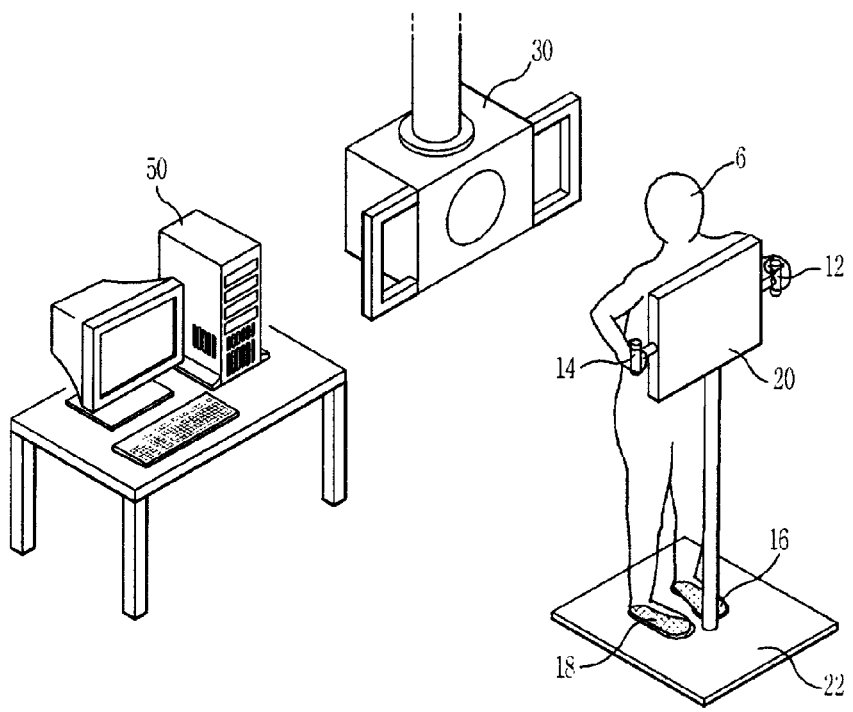
FIG. 2 is a view illustrating the configuration of the multiple-energy X-ray imaging apparatus according to the exemplary embodiment of the present invention.

Referring to FIG. 1, the multiple-energy X-ray imaging apparatus according to a first exemplary embodiment of the present invention includes an X-ray generating unit 30, a power supply unit 40, a detector unit 20, a sensor unit 10 and a host computer 50. The X-ray generating unit 30 sequentially radiates a plurality of X-rays to an object, which may be a patient or any other entity being evaluated using the multiple X-ray imaging system of the present invention. The power supply unit 40 is configured to supply the X-ray generating unit with operating power. The detector unit 20 converts the X-rays, which are radiated from the X-ray generating unit 30 and pass through the object, to electric signals. The sensor unit 10 is installed on a handle or other object that may be gripped by one or both hands of the object during an X-ray photography, as shown in FIG. 2 and described herein, to sense electrocardiogram signals that are generated from the pulsation of the heart of the object. The host computer 50 receives the electrocardiogram signals of the object from the sensor unit 10 in real time, and sequentially obtains X-ray images of different levels n of energy ranging the first energy to the $n^{th}$ energy, one X-ray image at a time, when an electrocardiogram signal having the same phase as the X-rays is generated.

The host computer 50 operates using predetermined software executing various control procedures to implement the system and method of the present invention. The host computer 50 may include a central processing unit (CPU), a memory, input and output devices such as the display unit 54 shown in FIGS. 2 and 4, and other components for implementing the various components and features described herein, for example, with reference to FIG. 4.

The X-ray generating unit 30 generates X-rays and radiates the generated X-rays to the object. The energy of X-ray is determined by the voltage and the current supplied to the power supply unit 40. A plurality of X-rays of different level of energy is radiated starting from the first energy X-ray to the $n^{th}$ energy X-ray.

When the power supply unit 40 provides the X-ray generating unit 30 with the voltage and current, the power supply unit 40 provides the voltage and the electric current based on a signal received from the host computer 50, so the host computer 50 controls the energy of each X-ray.

The detector unit 20 detects each X-ray, which passes through the object after being radiated from the X-ray generating unit 30. Each X-ray radiated from the X-ray generating unit 30 attenuates while passing through the object, and the X-ray transmission is different at each tissue of the object. Accordingly, the amount of transmission and attenuation of each X-ray is different at each portion of the object to which the X-ray is radiated. The tissues showing different X-ray transmission are roughly divided into gas; a soft tissue, such as an adipose tissue, muscles and blood; and a hard tissue containing, for example, a large amount of calcium, such as bones and teeth. X-ray signals detected by the detector unit 20 are converted to corresponding electrical signals transmitted to the host computer 50.

The sensor unit 10 is installed on a handle or other device that may be gripped by both hands of the object, as shown in FIG. 2. The sensor unit 10 senses the electrocardiogram signals generated according to the pulsation of the heart of the object in real time during the X-ray photography, and transmits the electrocardiogram signals to the host computer 50.

The host computer 50 controls the overall components of the multiple-energy X-ray imaging apparatus according to the present invention. The host computer 50 analyzes the electrocardiogram signal received from the sensor unit 10, and sends a signal to the power supply unit 40 such that a second energy X-ray image is obtained upon generation of an electrocardiogram signal having the same phase as the phase of an electrocardiogram signal provided at the point of time when the first energy X-ray image is obtained. Similarly, in obtaining the remaining X-ray images up to the nth X-ray image, the host computer 50 performs control procedures such that each X-ray image is obtained upon generation of an electrocardiogram signal having the same phase as the phase of an electrocardiogram signal provided at the point of time when the first energy X-ray image is obtained.

The electrocardiogram is a recording of an electrical change shown in the cardiac muscle during the cardiac cycle. The stimulation of the cardiac muscle starts from the venous sinus and proceeds to the atrium of the heart and the cardiac ventricles. Accordingly, by inducing the stimulation at two points in an ammeter, an action current of the heart is implemented into an electrical signal having a waveform which may be displayed on a graph. The electric signal obtained in this manner is referred to herein as an electrocardiogram signal. The electrocardiogram signal is obtained through a bipolar lead using both hands (lead I), the right hand and left foot (lead II), the left hand and left foot (lead III), the unipolar lead and the precordial lead, using standard electrodes placed on the object, such as a patient, according to conventions and arrangements known in the art. According to the first exemplary embodiment of the present invention, the electrocardiogram signal is obtained from lead I using both hands of the object.

FIG. 2 is a view illustrating the configuration of the multiple-energy X-ray imaging apparatus according to the embodiment of the present invention. For convenience sake, the following description will be made in relation to n=2, that is, the multiple-energy X-ray imaging apparatus generates the second energy X-ray in the last place.

In FIG. 2, the following description will be made in relation to an example arrangement for chest X-ray photography which is performed with an object such as a standing patient, and the first energy and the second energy represent a high energy and a low energy, respectively.

Referring to FIG. 2, the X-ray generating unit 30 is installed to radiate X-rays toward the detector unit 20 that is spaced away from the X-ray generating unit 30 by a predetermined distance. As shown in FIG. 1, the power supply unit 40 is connected to the X-ray generating unit 30 to provide the X-ray generating unit 30 with a voltage and an electric current such that X-rays having an X-ray energy corresponding to the voltage and the electric current are generated.

In this exemplary embodiment, the power supply unit 40 is controlled by the host computer 50 in that the power supply unit 40 provides a predetermined level of voltage and current that corresponds to a high energy and a lower energy. The predetermined voltage and current varies depending on the section or region of the object to be X-ray photographed on the basis that the transmission rate and attenuation rate are different for X-rays passing through air, bone and soft tissues. That is, bone tissue absorbs a larger amount of X-rays than soft tissues. The voltage and the current are determined in consideration that, since the lungs of a patient includes a large quantity of art, the tissues around the lungs do not show significant attenuation of X-rays.

An object 6 takes different poses according to each portion of the body to be X-ray photographed. For the chest X-ray photography according to the exemplary embodiment of the present invention shown in FIG. 2, the object 6 stands and is oriented to put the chest of the object onto or substantially adjacent to the detector unit 20 with the X-ray generating unit 30 at his/her back. The detector unit 20 detects any X-ray which is radiated from the X-ray generating unit 30 and passes through the object 6, converts the detected X-ray into an electric signal, and transmits the electric signal to the host computer 50, which is connected to the detector unit 20 as shown in FIG. 1.

The sensor unit 10 of FIG. 1 is installed on the detector unit 20, which may be implemented by a dual set of handles 12, 14, or other components which are used so that the object 6 may maintain a relatively fixed posture for the detector unit 20. As described above, if the object 6 puts his/her chest onto the detector unit 20 for X-ray photography and grips the dual handles 12, 14 with both hands, the electrocardiogram of the object 6 is sensed in real time and is transmitted to the host computer 50 during the X-ray photography. Each of the handles 12, 14 has electrodes for contacting the hands of the object 9, or for otherwise electrically communicating with the hands or other parts of the object 9. It will be understood that the object 9 may instead rest the hands, fingers, wrists, forearms, etc. of the object 9 onto or against the handles 12, 14, and that other components may be used instead of the dual set of handles 12, 14, such as handrests or other components adapted to electrically communicate with the associated parts of the object 9. For example, patients having arthritis in one or both hands, and thus unable to grip handles 12, 14 may instead rest their hands on the handles 12, 14 or handrests in order to allow electrodes in the handles 12, 14 or handrests to electrically communicate with the hands or other parts of the object 9 to perform electrocardiography with the object 9.

As described above, the sensor unit 10 according to the present invention is installed on or in the handles 12, 14, and the configuration of the X-ray imaging apparatus of the present invention is simplified compared to a conventional electrocardiogram apparatus, which has an additional electrode attached to the chest of an object. In addition, the X-ray imaging of the present invention is achieved if the object grips the handles 12, 14 without having to undress the upper body of the object, so that convenience of use is provided.

The host computer 50 receives the electrocardiogram signals of the object from the sensor unit 10, implemented in FIG. 2 as handles 12, 14. The host computer 50 obtains a second energy X-ray image upon generation of an electrocardiogram signal having the same phase as that of an electrocardiogram signal provided at the point of time when a first energy X-ray image is obtained.

In general, even though there is a need of objects 6 to be holding their breath during the X-ray photography, some objects 6 may fail to hold their breath. In addition, even if the object succeeds to hold his/her breath, the heart keeps pulsating, thereby causing an error to be experienced by prior art X-ray photography, with such errors occurring between the first energy X-ray image and the second energy X-ray image which are sequentially obtained.

According to the exemplary embodiment of the present invention, the first energy X-ray image and the second energy X-ray image are obtained when electrocardiogram signals of the object have the same phase, thereby minimizing the error caused by the breathing of the object or the pulsation of the heart.

The configuration of measuring the electrocardiogram of the object is shown in FIG. 2 as one embodiment of the present invention. The configuration of measuring the electrocardiogram is not limited thereof as long as the electrocardiogram is measured through a pair of dual handles 12, 14. According to another example, the electrocardiogram may be measured while having the object lie or sit during the X-ray photography.

When the X-ray photography is performed while having the object lie on a support, such as a bed, a handle may be provided on each of the lateral sides of the support. When the X-ray photography is performed while having the object sit on a support, such as a chair, a handle may be provided on each of the lateral sides of the support.

The position of the handle, such as handles 12, 14 in FIG. 2, is not limited thereto and may be implemented in various positions as long as each handle is reached by both hands of the object without difficulty.

FIGS. 3A to 3F show measurement of electrocardiograms of the object using at least one bipolar lead.

The bipolar lead represents the recording of a voltage difference between two electrodes as an absolute value. As per the prior art, the lead I has electrodes attached to both hands of the object 6, as shown in FIG. 3A; the lead II has electrodes attached to the left foot and the right hand of the object 6, as shown in FIG. 3C; and the lead III has electrodes attached to the left foot and the left hand of the object 6, such that each of the limb leads corresponds to the bipolar lead scheme known in the prior art.

Figure 3A:
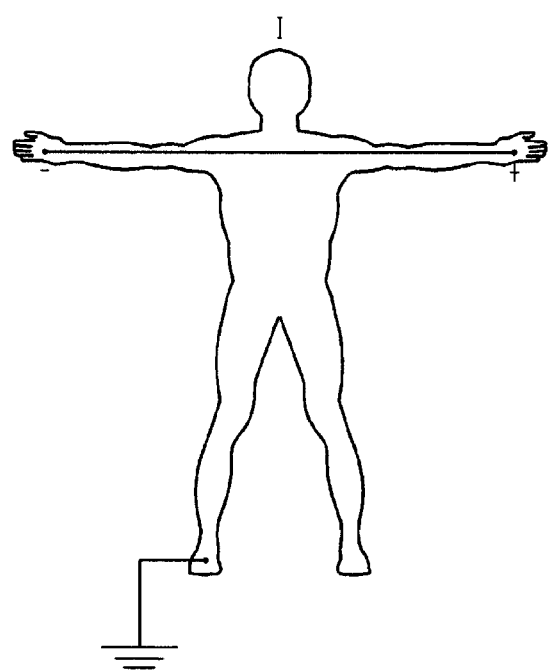
FIG. 3A is a view illustrating the placement of the lead I electrodes and ground electrode according to the prior art.
Figure 3B:
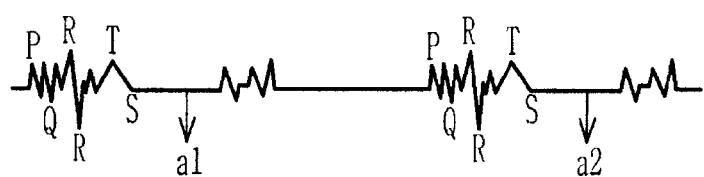
FIG. 3B is an electrocardiogram resulting from measurements by the electrodes of FIG. 3A, with the timing of generation of X-rays according to the present invention.

FIG. 3A is a view illustrating the measurement of an electrocardiogram according to the prior art using the lead I, in which the electrocardiogram signal is obtained from both hands of the object 6, with a resulting graph of an electrocardiogram shown in FIG. 3B. Referring to FIG. 3A, according to the use of lead I, the potential difference between the left hand and the right hand is recorded as an absolute value. The electric potential of the left hand is higher than that of the right hand and P, Q, R, S and T waves are periodically generated. According to this embodiment of the present invention, the first energy X-ray image and the second energy X-ray image are obtained when electrocardiogram signals have the same phase. That is, if the first energy X-ray image is obtained at the point of time of a1, the second energy X-ray image is obtained at the point of time of a2, as shown in FIG. 3B. Additional energy X-ray images when n is greater than 2 are obtained at other points of time in the electrocardiogram with the same phase as a1 and a2.

Figure 3C:
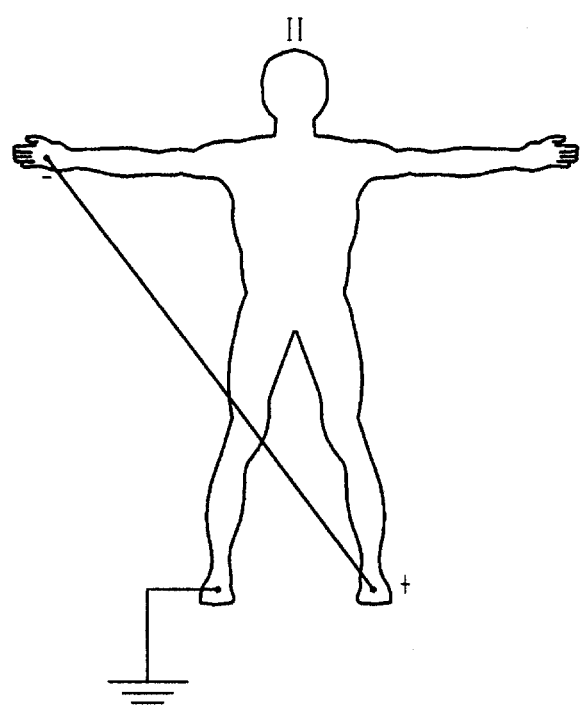
FIG. 3C is a view illustrating the placement of the lead II electrodes and ground electrode according to the prior art.
Figure 3D:
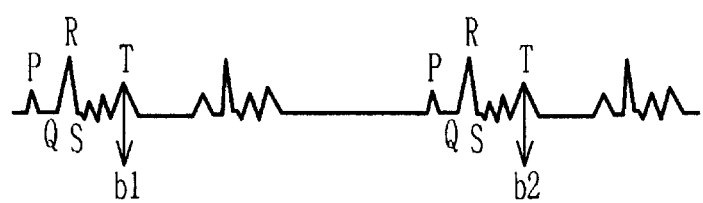
FIG. 3D is an electrocardiogram resulting from measurements by the electrodes of FIG. 3B, with the timing of generation of X-rays according to the present invention.

FIG. 3C is a view illustrating the measurement of an electrocardiogram according to the prior art using the lead II, in which the electrocardiogram signal is obtained from the left foot and the right hand of the object 6, with a resulting graph of an electrocardiogram shown in FIG. 3D. Referring to FIG. 3C, the potential difference between the left foot and the right hand is recorded as an absolute value. The electric potential of the left foot is higher than that of the right hand and P, Q, R, S and T waves are periodically generated. According to this embodiment of the present invention, the first energy X-ray image and the second energy X-ray image are obtained when electrocardiogram signals have the same phase. That is, if the first energy X-ray image is obtained at the point of time of b1, the second energy X-ray image is obtained at the point of time of b2. Additional energy X-ray images when n is greater than 2 are obtained at other points of time in the electrocardiogram with the same phase as b1 and b2.

Figure 3E:
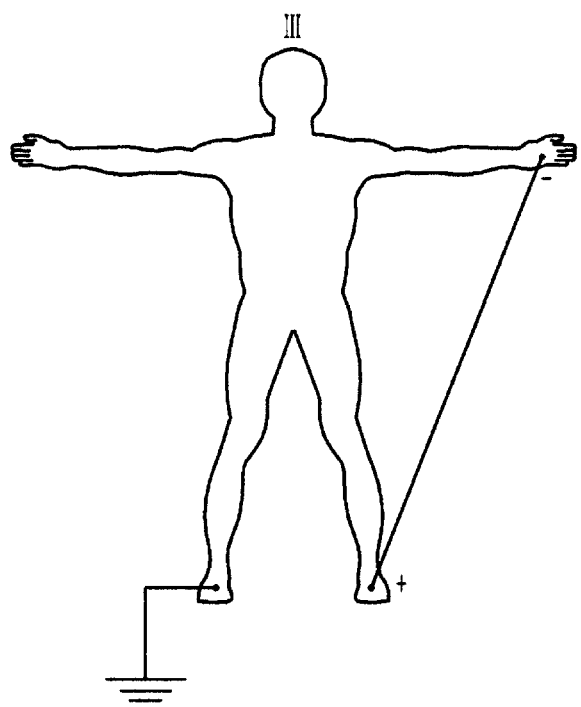
FIG. 3E is a view illustrating the placement of the lead III electrodes and ground electrode according to the prior art.
Figure 3F:
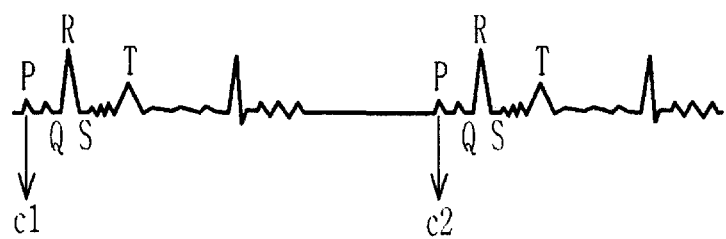
FIG. 3F is an electrocardiogram resulting from measurements by the electrodes of FIG. 3E, with the timing of generation of X-rays according to the present invention.

FIG. 3E is a view illustrating the measurement of an electrocardiogram according to the prior art using the lead III, in which the electrocardiogram signal is obtained from the left foot and the left hand of the object 6 with a resulting graph of an electrocardiogram shown in FIG. 3F. Referring to FIG. 3C, the potential difference between the left foot and the left hand is recorded as an absolute value. The electric potential of the left foot is higher than that of the left hand and P, Q, R, S and T waves are periodically generated. According to this embodiment of the present invention, the first energy X-ray image and the second energy X-ray image are obtained when electrocardiogram signals have the same phase. That is, if the first energy X-ray image is obtained at the point of time of c1, the second energy X-ray image is obtained at the point of time of c2. Additional energy X-ray images when n is greater than 2 are obtained at other points of time in the electrocardiogram with the same phase as c1 and c2.

In the exemplary embodiment, the electrocardiogram waveforms shown in FIGS. 3B, 3D, and 3F may have some differences in measured quantities such as amplitudes due to differences in measurements from the electrodes of leads I, II, and III, but FIGS. 3B, 3D, and 3F show a substantially identical result in quality.

According to a second exemplary embodiment of the present invention, the electrocardiogram signals are obtained from the left foot and the left hand of the object 6. Referring again to FIG. 2, the sensor unit 10 is installed on each of a left handle 12 and a foot device 16, such as a foot stool or base, or a single foot pad underneath at least one foot of the object 6. Accordingly, a patient as the object 6 standing on the foot device 16 with the foot pad underneath the bare foot of the patient has the bare foot in electrical communication with the foot device 16. As described herein, the foot device 16 may be implemented to contact only the left foot of the object 6.

According to a third exemplary embodiment of the present invention, the electrocardiogram signals are obtained from the left foot and the right hand of the object 6. In this case, referring again to FIG. 2, the sensor unit 10 is installed on each of a right handle 14 and the left foot device 16, such as a foot stool or base, or a single foot pad. As described herein, the foot device 16 may be implemented to contact only the left foot of the object 6. In an alternative embodiment, as described herein, a ground pad 18 may be included to contact only the right foot or right leg of the object 6. The foot device 16, the sensor unit 10 such as handles 12, 14, the ground pad 18, and the detector unit 20 may be implemented on a base 22 on which the object 6 stands, or alternatively lies or sits.

Alternatively, the sensor unit 10 may be installed on each of the left handle 12, the right handle 14, and the foot device 16. In this case, the measuring of the electrocardiogram may be selected among the lead I, the lead II, and the lead III depending on the status of the object 6 or the test conditions.

In the case that the X-ray photography is performed while having the object 6 lie down, for example, on a bed, or sit down, for example, on a chair, the electrocardiogram is measured through the lead II and the lead III by disposing the sensor unit 10 on a location reachable by the left foot of the object 6.

Independent of which lead is used among the lead I, the lead II and the lead III, there is no need to attach electrodes directly to the body of an object 6, thereby facilitating the measurement of the electrocardiogram.

The configuration of components of each of the multiple-energy X-ray imaging apparatuses according to the second and third embodiments of the present invention is identical to that of the first embodiment using the lead I except for the location of the sensor unit 10.

In alternative embodiments, ground electrodes may be used in a manner known in the art, such as shown in FIGS. 3A, 3C, and 3E, which may be attached to the right foot of the object, by convention used in the prior art. Accordingly, in the second and third exemplary embodiments of the present invention, the foot device 16 of the sensor unit 10 shown in FIG. 2 may be implemented such that only the left foot of the object 6 communicates electrically with the foot device 16, while the right foot of the object 6 is connected to a ground, as shown in FIGS. 3A, 3C, and 3E. In further alternative embodiments, the ground electrode may be implemented in a ground pad 18, as shown in FIG. 2, and/or may be placed on other parts of the body of the object 6 in a manner known in the art. Accordingly, in the second and third exemplary embodiments of the present invention, the foot device 16 in FIG. 2 may electrically communicate with at least the left foot of the object 6.

The multiple-energy X-ray imaging apparatus according to the exemplary embodiments of the present invention uses electrocardiogram signals of the object 6, thereby requiring signal processing for converting the electrocardiogram signals to digital signals. Accordingly, the multiple-energy X-ray imaging apparatus according to the exemplary embodiments of the present invention further includes a signal processing unit.

Figure 4:
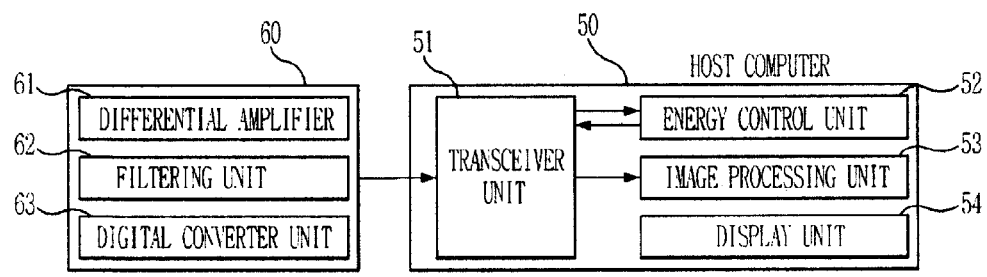
FIG. 4 is a block diagram illustrating a signal processing unit and a host computer of the multiple-energy X-ray imaging apparatus according to the exemplary embodiment of the present invention.

FIG. 4 is a block diagram illustrating a signal processing unit 60 and a host computer 50 of the multiple-energy X-ray imaging apparatus according to the exemplary embodiments of the present invention.

Referring to FIG. 4, the signal processing unit 60 performs a filtering and amplification on the electrocardiogram signal and coverts the electrocardiogram signal into a digital signal. The electrocardiogram signal, being an electric signal generated from the object, is generally very weak while the noise induced from surrounding electronic products or wires to the object 6 is relatively very strong. In order to amplify the electrocardiogram signal generated from the object 6 while removing the noise, the signal processing unit 60 includes a differential amplifier 61.

In addition, the signal processing unit 60 may further include a filtering unit 62 to prevent an offset voltage from being represented in the electrocardiogram signal having passed through the different amplifier 61 or to reduce the noise.

In addition, the signal processing unit 60 may further include an amplifier (not shown) to amplify the electrocardiogram signal having been subject to filtering. Alternatively, the amplifier may be incorporated into the filtering unit 62.

The signal processing unit 60 further includes a digital converter unit 63 to convert the electrocardiogram signals, having been subject to the above signal processing, into digital signals. Alternatively, the digital converter 62 may include the amplifier for amplifying the electrocardiogram signal prior to its digital conversion. The digital converter unit 63 sends the electrocardiogram signals, having been converted into digital signals, to the host computer 50.

The host computer 50 includes a transceiver unit 51, an energy control unit 52, an image processing unit 53 and a display unit 54. The transceiver unit 51 transmits and receives signals with respect to the signal processing unit 60, the detector unit 20, the sensor unit 10 and the power supply unit 40. The energy control unit 52 determines the point of time for generating the second energy X-ray based on the received electrocardiogram signal. For example, when time a2 in FIG. 3B is detected in the electrocardiogram signal by the control unit 52, corresponding to when the first energy X-ray is generated, the control unit 52 causes the X-ray generating unit 30 to generate the second energy X-ray at time a2. Similarly, when time b2 in FIG. 3C is detected in the electrocardiogram signal by the control unit 52, corresponding to when the first energy X-ray is generated, the control unit 52 causes the X-ray generating unit 30 to generate the second energy X-ray at time b2, and when time c2 in FIG. 3E is detected in the electrocardiogram signal by the control unit 52, corresponding to when the first energy X-ray is generated, the control unit 52 causes the X-ray generating unit 30 to generate the second energy X-ray at time c2. The image processing unit 53 generates an X-ray image based on the X-ray signal transmitted from the detector unit 20 and processed by the signal processing unit 60. The display unit 54 displays the image generated from the image processing unit 53.

The transceiver unit 51 is connected to the power supply unit 40 to provide control signals to the power supply unit 40 to supply the X-ray generating unit 30 with energy, with the control signals including data about the voltage and the electric current sent to the power supply unit 40, so that the X-ray generating unit 30 generates X-rays based on the voltage and electric current data. Accordingly, under the control of the host computer 50, the transceiver unit 51 is used to control the generation of X-rays by the X-ray generating unit 30. In addition, the transceiver unit 51 transmits the electrocardiogram signal of the object 6, which has been received from the signal processing unit 60, to the energy control unit 52, and receives an X-ray signal from the detector unit 20 and transmits the received X-ray signal to the image processing unit 53. Accordingly, the transceiver unit 51 acts as a communication interface between the various components of the multiple energy X-ray imaging system of the present invention.

The energy control unit 52 determines when to obtain the second energy X-ray image based on the electrocardiogram signal converted in the digital signal, using the times a2, b2, and c2 described and determined herein. The energy control unit 52 analyzes the electrocardiogram signals that are transmitted in real time, and sends, to the power supply unit 40, voltage and current signals, corresponding to the voltage and current data, for the second energy such that a second energy X-ray for the second energy X-ray image is radiated upon generation of an electrocardiogram signal having the same phase, that is, at times a2, b2, and c2, as the phase of an electrocardiogram signal provided at the point of time, such as times a1, b1, and c1, respectively, when the first energy X-ray image is obtained.

The image processing unit 53 receives an X-ray signal of the first energy and an X-ray signal of the second energy to generate the first energy X-ray image and the second energy X-ray image, respectively. The image processing unit 53 performs an image processing step, for example, a subtraction step using the first energy X-ray image and the second energy X-ray image by use of a weight based on the difference in an attenuation coefficient, thereby obtaining an image having a clearer bone region or an image having a clearer soft tissue region. Such image processing in the present invention may be implemented by Dual-Energy X-ray Absorptiometry (DEXA), which is well-known, and the detailed description thereof will be omitted.

The display unit 54 outputs the image generated from the image processing unit 53, so that a heath condition of the object 6 may be diagnosed.

Hereinafter, a method of controlling a multiple-energy X-ray imaging apparatus according to the exemplary embodiments of the present invention will be described with reference to FIG. 5.

FIG. 5 is a flowchart showing a method of controlling a multiple-energy X-ray imaging apparatus according to the exemplary embodiments of the present invention. The following description will be made with reference to a chest X-ray photography being performed while the object stands in front of the detector unit to closely put the chest onto the detector unit 20, as shown in FIG. 2. The first energy and the second energy represent a high energy and a low energy, respectively.

Referring to FIG. 5, first, the electrocardiogram of the object is measured in step 100. The measuring of the electrocardiogram of the object is achieved through the dual handle 12, 14 using the lead I electrodes or at least one of the handles 12, 14 and the foot device 16 or stool using the lead II or lead III electrodes. The measured electrocardiogram signals are transmitted to the host computer 50 and then are converted into digital signals. The measuring of the electrocardiogram signals is achieved in real time until the X-ray photography is finished.

An X-ray energy having a high energy is radiated to the object to obtain an X-ray image corresponding to the high energy in step 110. The image obtained from using the high energy X-rays is obtained by providing the X-ray generating unit 30 with a voltage of 110 peak kilovoltage (kVp) and an electric current of 120 Ma that are suitable to generate the high energy X-ray for the chest photography. Note that high energy and low energy used in the present invention are relative and are set according to the portion to be diagnosed. For example, high energy corresponds to 110 kVp, 120 mA, 0.2 seconds and low energy corresponds to 60 kVp, 200 mA, 0.2 seconds.

The measured electrocardiogram signals are analyzed in step 120 to determine the phase of an electrocardiogram signal provided at the point of time, such as a1 in FIG. 3B, when the X-ray image of the high energy is obtained. The analyzing of the electrocardiogram signal and the determining of the phase are performed by the host computer 50. The analyzed electrocardiogram signal is an electrocardiogram signal converted to be in the form of a digital signal.

An X-ray of a low energy is radiated upon generation of an electrocardiogram signal having the same phase as that of the electrocardiogram signal provided at the point of time, such as a2 in FIG. 3B, when the X-ray image of the high energy was previously obtained, so that an X-ray image of a low energy is obtained in step 130. To this end, a voltage of 60 kVp and an electric current of 200 mA suitable to generate the low energy X-ray for the chest photography are provided to the X-ray generating unit 30. The chest X-ray photography is affected by the pulsation of the heart which may cause differences among the X-ray images sequentially taken. However, according to the present invention, the high energy X-ray image and the low energy X-ray image are obtained only when electrocardiogram signals having the same phase are generated, that is, at times a1 and a2 in FIG. 3B, for example, thereby preventing the pulsation of the heart from reducing the quality of the X-ray imaging.

A bone region and a soft tissue region are separated from the high energy X-ray image and the low energy X-ray image in step 140. The separating of the bone and soft tissue images from the high energy X-ray image and the low energy X-ray image may be implemented by Dual-Energy X-ray Absorptiometry (DEXA), in which a weight is calculated by use of the attenuation coefficient of each of the bone and the soft tissue, and then an algebraic operation is performed on the two images using known image processing methods.

The description made with reference to FIG. 5 represents only one embodiment of the present invention. Alternatively, the first energy and the second energy may represent a low energy and a high energy, respectively. In addition, the voltage and the electric current provided to the power supply unit 40 are not limited to the above embodiment, and may be provided in different ranges.

The above-described apparatus and methods according to the present invention can be implemented in hardware, firmware or as software or computer code that can be stored in a recording medium such as a CD ROM, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered in such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Although a few exemplary embodiments of the present invention have been shown and described, it will be appreciated by those skilled in the art that various changes in form and details may be made in these exemplary embodiments without departing from the principles and the spirit and scope of the invention, as defined in the appended claims and their equivalents.

What is claimed is:

1. A multiple-energy X-ray imaging apparatus comprising:
an X-ray generating unit configured to sequentially radiate X-rays starting from a first energy X-ray of first energy level to a $n^{th}$ energy X-ray of $n^{th}$ energy level;
a power supply unit configured to supply the X-ray generating unit with power;
a detector unit configured to detect the X-rays, which are radiated from the X-ray generating unit, and to convert the detected X-rays to electric signals;
a handle mounted on the detector unit to be gripped by an object;
a sensor unit installed on the handle to sense an electrocardiogram signal generated from the object; and
a host computer configured to obtain X-ray images by performing control procedures such that each of at least one X-ray starting from a second energy X-ray to an $n^{th}$ energy X-ray is sequentially radiated upon generation of the electrocardiogram signal that has a same phase as the phase of the electrocardiogram signal provided at a point of time when an image based on the first energy X-ray is obtained.

2. The multiple-energy X-ray imaging apparatus of claim 1, wherein the sensor unit comprises a left hand electrode, a right hand electrode, and a ground electrode.

3. The multiple-energy X-ray imaging apparatus of claim 1, further comprising a signal processing unit configured to perform a filtering and an amplification on the electrocardiogram signal and to convert the electrocardiogram signal into a digital signal such that the electrocardiogram signal sensed by the sensor unit is analyzed.

4. The multiple-energy X-ray imaging apparatus of claim 3, wherein the host computer comprises a transceiver unit configured to receive X-ray signals from the detector unit, to receive the electrocardiogram signal, which has been converted into the digital signal, from the signal processing unit, and to transmit a control signal to the X-ray generating unit and a power source supply unit.

5. The multiple-energy X-ray imaging apparatus of claim 4, wherein the host computer further comprises an energy control unit configured to receive the electrocardiogram signal, which has been converted into the digital signal, in real time and to determine an X-ray image for obtaining a first and at least a second time points such that the X-ray images are obtained by sequentially radiating each of the X-rays starting from the second energy X-ray to the $n^{th}$ energy X-ray upon generation of the electrocardiogram signal that has a same phase at the at least second time points as a phase of the electrocardiogram signal provided at of the first time point when an image based on the first energy X-ray is obtained.

6. The multiple-energy X-ray imaging apparatus of claim 4, wherein the host computer further comprises an image processing unit configured to generate a plurality of X-ray images and to separate a bone region and a soft tissue region from the generated plurality of X-ray images by receiving the X-ray signals through the transceiver unit.

7. The multiple-energy X-ray imaging apparatus of claim 1, wherein n is 2, and wherein the first energy represents a high energy and the second energy represents a low energy.

8. The multiple-energy X-ray imaging apparatus of claim 1, wherein the sensor unit is further installed on a foot stool that makes contact with a foot of the object.

9. A method of controlling a multiple-energy X-ray imaging apparatus, the method comprising:
measuring an electrocardiogram signal using a sensor unit which is installed on a handle which is mounted on a detector unit to be gripped by an object;
obtaining a first energy X-ray image by radiating a first energy X-ray;
determining a phase at a point of time when the first energy X-ray image is obtained by analyzing the measured electrocardiogram signal; and
obtaining X-ray images by sequentially radiating each of at least one X-ray starting from a second energy X-ray to a $n^{th}$ energy X-ray upon generation of the electrocardiogram signal that has a same phase as the determined phase.

10. The method of claim 9, wherein the measuring of the electrocardiogram signal is performed by sensing an electrocardiogram signal through the sensor unit, which is installed on a dual handle.

11. The method of claim 9, wherein the measuring of the electrocardiogram signal is performed by sensing a first electrocardiogram signal through a first sensor unit, which is installed on the handle that is grippable by a right hand of the object, and a second sensor unit, which is installed on a foot stool making contact with a left foot of the object.

12. The method of claim 9, wherein the measuring of the electrocardiogram signal is performed by sensing a first electrocardiogram signal through a first sensor unit, which is installed on the handle that is grippable by a left hand of the object, and a second sensor unit, which is installed on a foot stool making contact with a left foot of the object.

13. The method of claim 9, wherein attenuation coefficients of bone and soft tissue are calculated from the first energy X-ray image and the at least second X-ray image; and wherein images of a bone region and the soft tissue are separated from the obtained X-ray images by use of a difference of a calculated attenuation coefficients.

14. A multiple-energy X-ray imaging apparatus comprising:
an X-ray generating unit configured to sequentially radiate a plurality of X-rays including a first energy X-ray having a first energy level and a second energy X-ray having a second energy level;
a detector unit configured to detect the plurality of X-rays, and to convert the detected X-rays to electric signals;
a handle mounted on the detector unit to be gripped by an object;
a sensor unit installed on the handle to sense an electrocardiogram signal generated from the object; and
a host computer to determine a first time point of the electrocardiogram signal having a phase, to cause the X-ray generating unit to radiate the first energy X-ray to generate a first X-ray image, to determine a second time point of the electrocardiogram signal having a same phase, and to cause the X-ray generating unit to sequentially radiate the second energy X-ray at the second time point to generate a second X-ray image.

15. The multiple-energy X-ray imaging apparatus of claim 14, wherein the sensor unit comprises a foot electrode.

16. The multiple-energy X-ray imaging apparatus of claim 14, further comprising a signal processing unit configured to filter the electrocardiogram signal and to covert the electrocardiogram signal into a digital signal analyzed by the host computer to determine a first and at least a second time points having the same phase.

17. The multiple-energy X-ray imaging apparatus of claim 16, wherein the host computer further comprises an energy control unit configured to receive the digital signal in real time for determining the first and second time points.

18. The multiple-energy X-ray imaging apparatus of claim 16, wherein the host computer further comprises an image processing unit configured to generate the first and the second X-ray images, and to separate a bone region and a soft tissue region from the generated X-ray images.

19. The multiple-energy X-ray imaging apparatus of claim 14, wherein the first energy level has a magnitude greater than the second energy level.

* * * * *